United States Patent [19]

Schilperoort et al.

[11] Patent Number: 4,693,976
[45] Date of Patent: Sep. 15, 1987

[54] PROCESS FOR THE INCORPORATION OF FOREIGN DNA INTO THE GENOME OF DICOTYLEDONOUS PLANTS USING STABLE COINTEGRATE PLASMIDS

[76] Inventors: Robbert A. Schilperoort, Anthonie Duycklaan 10c, 2334 CD Leiden; Jacques Hille, Reymerweg 76, 6871 HG Renkum, both of Netherlands

[21] Appl. No.: 583,024

[22] Filed: Feb. 23, 1984

[30] Foreign Application Priority Data

Feb. 24, 1983 [NL] Netherlands ................. 8300699

[51] Int. Cl.$^4$ ............. C12P 21/00; C12P 21/02; C12N 1/22; C12N 1/00
[52] U.S. Cl. ........................ 435/172.3; 435/68; 435/70; 435/253; 435/320; 47/58; 935/30; 935/56; 935/64; 935/67
[58] Field of Search ........... 435/68, 70, 172.2, 172.3, 435/253, 317; 47/58; 935/32, 56, 64, 67

[56] References Cited

PUBLICATIONS

Hooykaas et al, Plasmid vol. 4, pp. 64–75, "Molecular Mechanism of Ti Plasmid Mobilization by R Plasmids: Isolation of Ti Plasmids with Transposer Insertions in Agrobacterium-Tumetusciens.
Hille et al, Abstract P-40 Symposium University Bielefeld Autumn 1982, "Onc and Vir Genes Located on the Ti-Plasmid of Agrobacterium Tumefaciens".
Leemans et al, J Mol Appl Genet, vol. 1(2), 1981, "Site-Specific Mutagenesis of Agrobacterium Ti Plasmids and Transfer of Genes to Plant Cells".
Schell et al in Genetic Eng to Biotech 1982 "The Use of Ti Plasmids as Gene Vectors for Plants" pp. 41–53.
Hille et al Plasmid vol. 7, pp. 107–118, 1982 "Construction and Application of R Prime Plasmids . . . for Complementation of vir Genes".
Ruvkun et al, Nature, vol. 289, pp. 85–88, 1981.
White et al, Proc Natl Acad Sci, vol. 79, May 1982, pp. 3193–3197, "Tumor Induction by . . . to the Plant Genome".
Molecular Genetics of the Bacteria-Plant Interaction, pp. 223–228, Symposium Plasmid vol. 7 pp. 107–118 (1982) J. Hille et al.
Journal of Bacteriology, vol. 154, May 1983 J. Hille et al.

Primary Examiner—Thomas G. Wiseman
Assistant Examiner—Robin Lyn Teskin
Attorney, Agent, or Firm—Ladas & Parry

[57] ABSTRACT

The invention relates to a process for the incorporation of foreign DNA into the genome of dicotyledonous plants by infecting the plants or incubating plant protoplasts with Agrobacterium tumefaciens bacteria, which contain one or more Ti (tumour inducing) plasmids, wherein as Ti plasmid a stable cointegrate plasmid composed of the plasmid R772 and the plasmid pTiB6 with foreign DNA incorporated in the T-region of the Ti component of the cointegrate plasmid is applied as well as to a cointegrate plasmid pAL969 and cointegrate plasmids derived from the cointegrate plasmid by the incorporation of foreign DNA into the T-region of the Ti component.

3 Claims, 7 Drawing Figures

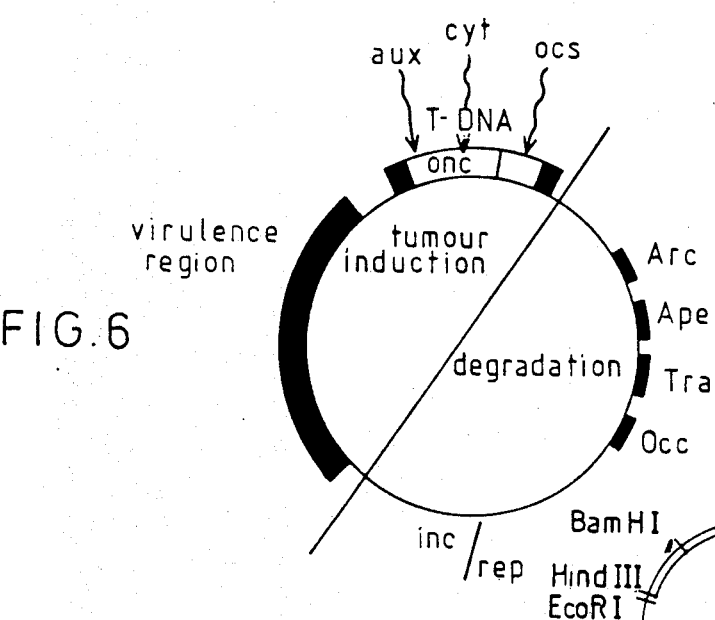
FIG. 2
FIG. 6
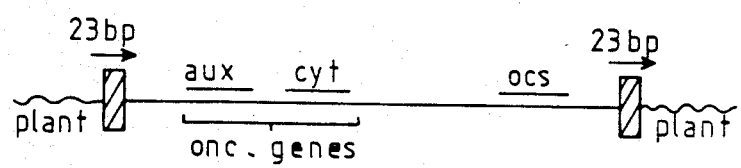
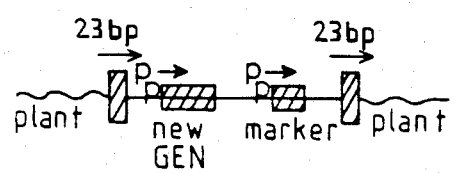
FIG. 7

PROCESS FOR THE INCORPORATION OF FOREIGN DNA INTO THE GENOME OF DICOTYLEDONOUS PLANTS USING STABLE COINTEGRATE PLASMIDS

The invention relates to a process for the incorporation of foreign DNA into the genome of dicotyledonous plates by infecting the plants or incubating plant protoplasts with *Agrobacterium tumefaciens* bacteria, which contain one or more Ti-(tumour inducing)plasmids.

It is known that the Ti plasmid of *A. tumefaciens* is essential for the capcity of this bacterium to cause the formation of tumours that are called "Crown gal" on dicotyledonous plants (Van Larebeke et al, Nature (London) 252, 169-170 (1974); Watson et al, J. Bacteriol. 123, 255-264 (1975); Zaenen et al, J. Mol. Biol. 86, 109-127 (1974). Part of this plasmid, designated as the T-region is integrated as T-DNA in the plant genome during tumour induction (the chromosomal DNA) (Chilton et al, Cell 11, 263-271 (1977); Chilton et al, Proc. Nat. Acad. Sci. U.S.A. 77, 4060-4064 (1980); Thomashow et al, Proc. Nat. Acad. Sci. U.S.A. 77, 6448-6452 (1980); Willmitzer et al, Nature (London) 287, 359-361 (1980) and is expressed in various RNA-transcripts (Drummond et al, Nature (London) 269, 535-536 (1977); Ledeboer, thesis Governmental University of Leyden(78); Gurley et al, Proc. Nat. Acad. Sci. U.S.A. 2828-2832 (1979); Willmitzer et al, Mol. Gen. Genet. 182, 255-262 (1981)). The tumour cells show a phytohormone independent growth and contain one or more unusal aminoacid derivatives, known as opines, of which octopine and nopaline are best-known. The T-region of an octopine Ti plasmid carries a gene, which codes for the enzyme lysopine dehydrogenase (LpDH) or octopine synthase (OCS) which the tumour cell needs for the synthesis of octopine (Schröder et al, FEBS Lett. 129, 166-168 (1981)). The plasmid furthermore contains genes for the catabolism of these opines by the bacterium (Bomhoff et al, Mol. Gen. Genet. 145, 177-81 (1976); Montoya et al, J. Bacteriol. 129, 101-107 (1977). If the T-region on the plasmid is lacking, no tumours are induced (Koekman et al, Plasmid 2, 347-357 (1979)). In addition to the T-region another region on the Ti plasmid appears to be essential for the tumour inducing capacity of the bacterium (Garfinkel et al, J. Bacteriol. 144, 732-743 (1980); Ooms et al, J. Bacteriol. 144, 82-91 (1980)), which part, however, has never been found in the plant tumour cells. This region with a size of about 20 Md, in which mutations appear to be complementary in trans, is called the vir-(virulence)-region (Hille et al, Plasmid 6, 151-154 (1981); Hille et al, Plasmid 7, 107-118 (1982); Klee et al, J. Bacteriol. 150, 327-331 (1982)).

It will be clear from the above that the procaryotic bacterium *A. tumefaciens* has a system for genetic manipulations of eucaryotic plants present in nature. The T-DNA-region of the Ti plasmid appears to be suitable for the incorporation of foreign DNA, in particular genes which code for particular desirable properties, into the genome of plant cells, the more so as in principle it is possible to eliminate the genes which are the cause of the tumour without simultaneously blocking the incorporation of the new genes. A first possibility seems to be to transform plant cells by infecting plants with *A. tumefaciens* bacteria which contain one or more Ti plasmids, the T-region of which is manipulated in the desirable manner. It is even better to incubate plant protoplasts with such *A. tumefaciens* bacteria.

For practical resons the introduction of new genes in the T-region by means of recombinant-DNA techniques are preferably carried out in *Escherichia coil*. However, the Ti plasmid normally cannot be maintained in *E. coli* (it does not replicate in this host). So, in the existing procedures a so-called shuttle vector is used which replicates in *E. coli* and *A. tumefaciens* and into which the T-region is introduced. Subsequently new genes are introduced into this T-region. However, the complete Ti plasmid is necessary in order to transform cells via *A. tumefaciens*. The reason is that the Ti plasmid contains the essential vir-region on which genes are positioned which see to a selection of T-DNA (presumably by recognition of base sequences at the extremites of this T-region) and the transfer to the plant.

Since the Ti plasmid does not maintain its position in *E. coli* in the existing procedures, the shuttle vector with the manipulated T-region is transferred to an *A. tumefaciens* which contains a complete Ti plasmid which can co-exist with the shuttle vector. Since the shuttle vector contains T-DNA parts which are also present in the T-region of the Ti plasmid a double crossing-over between the homologous parts of both T-regions is forced. Therewith the new genes are incorporated into the T-region of the intact Ti plasmid.

Existing procedures for the site directed mutation of Ti plasmids are described by Leemans et al, The Embo Journal 1, 147-152 (1982); Matzke et al, J. Mol. Appl. Genet. 1, 39-49 (1981); vide for the general principle, on which these techniques are based, Ruvkun et al, Nature (London) 289, 85-88 (1981). The last step of the Ti plasmid mutation is always performed in Agrobacterium itself, because the host range of Ti plasmids is restricted to Rhizobiaceae. After a cloned fragment of the Ti plasmid in *E. coli* has been mutated for instance by insertion of a transposon, the mutated fragment is subcloned on a vector with a broad host range and transferred into a Ti plasmid containing Agrobacterium strain. Herein the inserted DNA is incorporated by homologous recombination via double crossing-over into the Ti plasmid, whereupon either the plasmid with a broad host range is destroyed by means of a in compatible plasmid or the Ti plamid is transferred to another Agrobaceterium by conjugation. By investigation of the transconjugants it is checked whether the correct mutation of the Ti plasmid has taken place.

These known procedures are rather laborious and given technical problems, which could be avoided of the site directed mutation of the Ti plasmid itself could directly be performed in *E. coli*. However, the Ti plasmid is lacking an origin of replication or a replicator which can function in *E. coli*.

The invention is present in the use of a stable cointegrate plasmid, obtained from a Ti plasmid (pTiB6) and an antibiotic resistance plasmid having a broad host range (R772). Cointegrate plasmids are obtained by mobilisation of the octopine Ti plasmid pTiB6 with the Inc.P-1 type plasmid, R772, as described by Hooykaas et al, Plasmid 4, 64-75 (1980). Thanks to the broad host range of the R772 component the cointegrates can replicate both in *A. tumefaciens* and in *E. coli* but mostly they are not stable: during transfer of *A. tumefaciens* to *E. coli* dissociation occurs, whereupon the Ti component of the cointegrate gets lost. However, the efforts have been successful to isolate a cointegrate plasmid which is stable for both types of bacteria: the R772::pTiB6 cointegrated plasmid pAL969, the existence of which was disclosed by Hille et al, Plasmid, 7, 107–118 (1982).

This stable cointegrate plasmid opens the possibility to follow a new process in which all the steps needed for incorporating new genes into the T-region of the intact Ti plasmid are carried out in *E. coli* whereupon the cointegrate plasmid with the manipulated T-region is transferred into an *A. tumefaciens* without a Ti plasmid of its own. Agrobacterium strains which contain such a cointegrate plasmid are capable of inducing tumours on various types of plants or more in general of incorporating foreign DNA into chromosomes of plants, in particular dicotyledonous plants, such as tomato, tobacco, petunia, potato, sugarbeet, sunflower, leguminous plants, and the like.

The invention therefore provides a process of the type mentioned at the beginning, which is characterized in that as Ti plasmid a stable cointegrate plasmid derived from a plasmid R772 and a plasmid pTiB6 with foreign DNA incorporated into the T-region of the Ti component of the cointegrate plasmid, is applied.

The invention also provides a cointegrate plasmid pAL969 and cointegrate plasmids derived therefrom by the incorporation of foreign DNA in the T-region of the Ti component of the cointegrate plasmid.

The invention also provides a process for the production of *Agrobacterium tumefaciens* bacteria, which contain one or more Ti plasmids, which is characterized in that a vector known per se for use in *Escherichia coli* provided with a T-region in which foreign DNA is incorporated, in combined in *E. coli* as a host with the cointegrate plasmid pAL969 or cointegrate plasmid derived therefrom by incorporation of foreign DNA in the T-region of the Ti component, whereafter the cointegrate plasmid, with the foreign DNA provided to the vector incorporated by double crossing-over in the T-region of the Ti component of the cointegrate plasmid is transferred, to an *A. tumefaciens* which does not itself carry a plasmid belonging to the same incompatibility groups as the two different components of the Ris Ti cointegrate. The invention also provides plants and plant cells obtained after the genetic properties of the original plants c.q. plant cells have been modified, applying the process according to the invention.

The use of the process according to the invention, in which plants or plant cells having modified genetic information are obtained may be present in the improvement of plants (cultivation of an improved species, which for instance is better resistant to herbicides), as well as in the realization of a bioreactor, for fermentation of plant cells, optionally immobilised thereupon, which produce a specific desirable translation product, for instance enzyme, or a secondary metabolite of the plant cell, in large quantities.

The process according to the invention therefore offers the possibility to manfacture mutants of higher plants having well defined genetically improved resp. modified properties in an otherwise unchanged background. As already remarked before this is vital to the plant breeding industry, the more so as from the tissue lines which are obtained with application of the process according to the invention regenerates can be obtained at an early stage after transformation. Furthermore, the cells with autotrophic growth which are obtained with application of the process according to the invention, for instance the Crown gall cells, only need a very simple synthetic medium for a good growth in a fermentator, to which medium i.a. no phytohormones need to be added. Cells thus obtained, in which foreign DNA is introduced, can be cultures on a large scale for the production of those substances, for which the foreign DNA codes, such as alkaloids, aminoacids, hydrocarbons, proteins, enzymes, steroids etc. (cf. Impact of Applied Genetics, Micro Organisms, Plants and Animals. OTA Report, Congress of the United States Office of Technology Assessment, Washington 1981).

*E. coli* has a much higher rate of growth than *E. tumefaciens,* whilst many mutants are available and special cloning carriers, such as a cosmids and vectors in which gene activation can occur.

The process according to the invention does not require shuttle vectors with a broad host range, which often are too big for recombinant DNA activiates and often do not have the correct restriction enzyme sites for insertion of the T-region. In the procedure according to the invention in *E. coli* the well-known and usable vectors (specific for *E. coli*) are used. Such a vector with the T-region, in which new genes have been incorporated, in combinated in *E. coli* with the stable R::Ti cointegrate to have the double crossing-over take place, in consequence of which the new genes are incorporated into the T-region of the Ti component of the cointegrate. As already described before then the manipulated R::Ti cointegrate is transfer to *A. tumefaciens* which takes place at high frequency.

It seems that the procedure can be simplified by making use of polAts strains (ts=temperature sensitive). In such strains most of the vectors (plasmids) developed for *E. coli,* which are derived from the colE1 plasmids, can replicate at 32° C., but not at 42° C., though other plasmids, such as the cointegrate plasmid pAL969 are maintained at both temperatures. By a simple selection, at for instance a marker for antibiotic resistance at 42° C. one would directly obtain the strains which only carry the site directed mutation, e.g. insertion of foreign DNA, in the cointegrate plasmid.

An *E. coli* strain, with in it the stable cointegrate plasmid pAL969, is deposited and available at the Centraalbureau voor Schimmelculters (CBS) at Baarn, the Netherlands, deposited on Feb. 24, 1983 under No. CBS 190.83.

The invention is illustrated with the aid of the drawing in which:

FIG. 2 shows a physical card of the plasmid pRL246;

FIG. 6 shows in outline an octopine Ti plasmid and

FIG. 7 shows in outline the structure of normal T-DNA and of manipulated "artificial" T-DNA, as incorporated in the plant genome, as well as with the aid of a description of experiments carried out.

The illustration is subdivided into:

Figure 1:
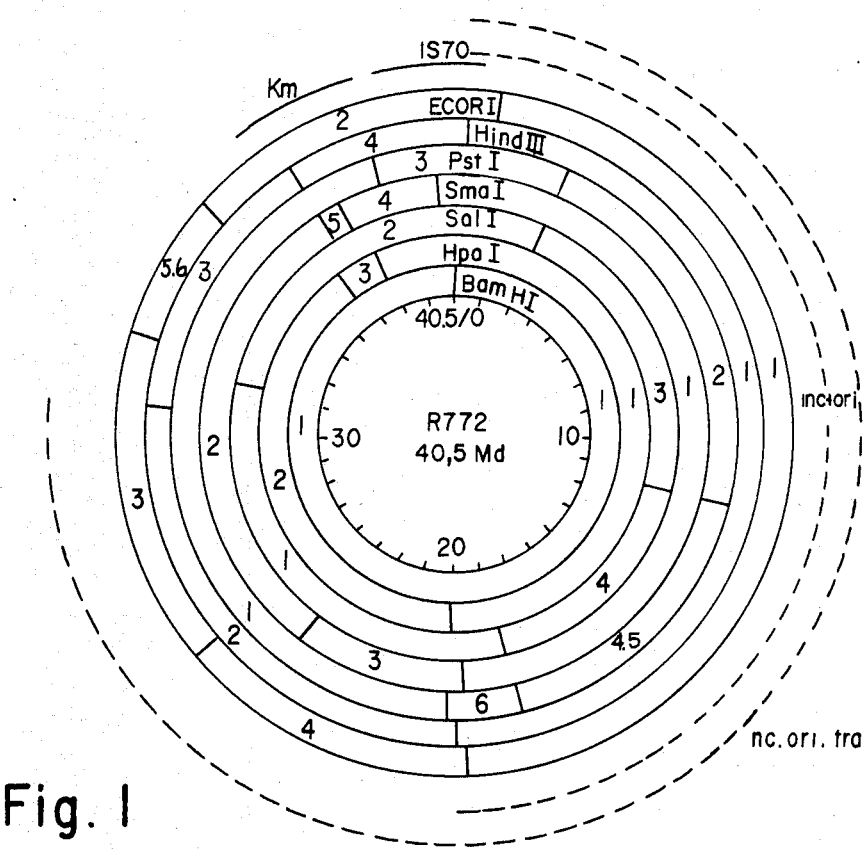
FIG. 1 shows a physical card of the plasmid R772.

A. construction of a physical map of the stable cointegrate plasmid pAL969;

B. model experiment for site directed mutation of R772.

Finally there is an example of the process according to the invention where a site directed mutation of the T-region was carried in the Ti component of the cointegrate plasmid pAL969 and the phenotype of the mutation was examined with divers plant species.

The strains and plasmids used are listed in the following table A.

TABLE A

Bacterium strains and plasmids used

| strains | relevant phenotype | plasmids | Source |
|---|---|---|---|
| *E. coli* | | | |
| KMBL1164 | pro⁻, thi⁻ | | Van de Putte |
| KMBL1001 | — | | Van de Putte |
| *A. tumefaciens* | | | |
| LBA 937 | Rif$^r$, Nar$^r$ | R772, pTiB6 | Hooykaas et al. Plasmid 4, 64–75 (1980) |
| LBA973 | Gen$^r$, Nov$^r$ | pAL969 | Hooykaas |
| LBA1831 | Rif$^r$, Nal$^r$ | pAL1831 | described herein |

| Plasmids | relevant phenotype | Source |
|---|---|---|
| R772 | Km$^r$ | Hedges |
| pAL969 | Km$^r$ | Hooykaas |
| pAL 1831 | Km$^r$, Ap$^r$, Cm$^r$ | described herein |
| pRAL3501 | Tc$^r$, Cm$^r$ | described herein |
| pRL220 | Tc$^r$, Cm$^r$, Ap$^r$, Sm$^r$ | Hille and Schilperoort. Plasmid 6, 30–362 (1981) |
| pRL220 | Tc$^r$, Ap$^4$, Cm$^r$ | described herein |

Clones derived from R772

| Plasmid | Restriction fragment | Vector | Relevant phenotype | Source |
|---|---|---|---|---|
| pRL231 | HindIII—4 | pTR262 | Tc$^r$ | described herein |
| pRL232 | HindIII—3 | pTR262 | Tc$^r$ | described herein |
| pRL233 | HindIII—3+4 | pTR262 | Tc$^r$, Km$^r$ | described herein |
| pRL236 | EcoRI—1+2 | — | Km$^r$, Inc-P | described herein |
| pRL237 | EcoRI—2 | pBR322 | Ap$^r$, Tc$^r$, Km$^r$ | described herein |
| pRL238 | HindIII—1+2 | pTR262 | Tc$^r$, Inc-P | described herein |
| pRL247 | PstI—6 | pBR325 | Cm$^r$, Tc$^r$ | described herein |
| pRL248 | PstI—3 | pBR325 | Cm⁻, Tc$^r$ | described herein |
| pRL246 | pBR322::IS70 | — | Ap$^r$, Tc$^r$ | described herein |
| pRL239 | — | — | Km$^r$, Ap$^r$, Cm$^r$, Inc-P | described herein |

The conjugations were performed in conformity with the specification by Hille et al, Plasmid 7, 107–118 (1982).

The plasmid isolation occurred for *E. coli* as described by Birnboim and Doly, Nucl. Ac. Res. 7, 1513–1523 (1979) and for *A. tumefaciens* as described by Koekman et al, Plasmid 4, 184–195 (1980).

Clearage with restriction endonucleases, agarose gel electrophoresis, Southern blotting and DNA-DNA filter hybridisation were performed as described by Prakash et al, J. Bacteriol. 145, 1129–1136 (1981).

The ligation of restriction fragments was carried out in 6.5 mM MgCl$_2$; 60 mM Tris-HCl pH 7.6; 10 mM dithiothreitol and 0,4 mM ATP for 20 hours at 14° C. The DNA concentration in the ligation mixture was usually about 100 /μgr per ml, with an excess of five times of the DNA to be cloned with regard to the vector DNA. After ligation the mixture was immediately used for transformation.

Transformation of *E. coli* cells occurred by means of the CaCl$_2$ method described by Cohen et al, Proc. Nat. Acad. Sci. 69, 2110–2114 (1972).

A. Construction of a physical card of the stable cointegrate plasmid pAL969

Figure 3:
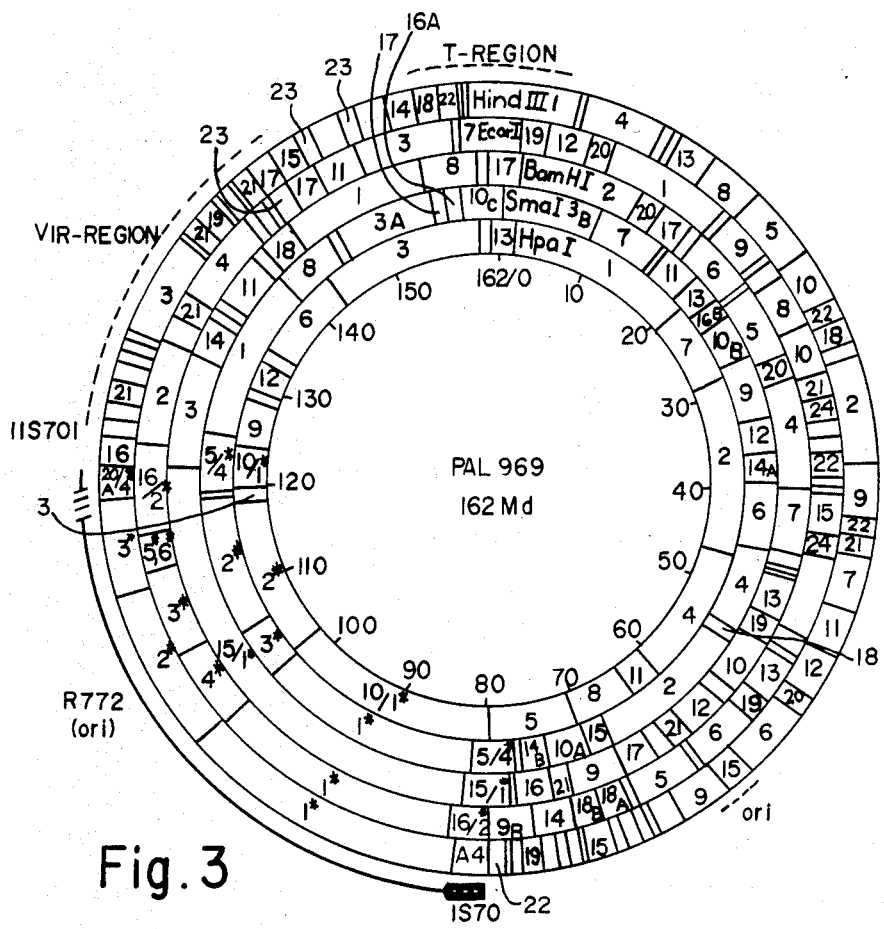
FIG. 3 shows a physical card of the cointegrate plasmid pAL969.

In experiments described by Hooykaas et al, Plasmid 4, 64–75 (1980), in which an octopine Ti plasmid pTiB6) was mobilized with the Inc.P-1 type plasmid R772 with a broad host range, a particular R772::Ti cointegrate plasmid (pAL969) was obtained. When strains which contain this plasmid were used as donor in further crossings, 100% cotransfer of R772 and Ti plasmid markers could be shown, i.e. 100% cotransfer in case of transfer from *E. coli* to *A. tumefaciens* and v.v., the R::Ti cointegrate kept stable in both *E. coli* and *A. tumefaciens* and so did not desintegrate into the composite plasmids. In order to obtain insight into the stability of this cointegrate plasmid observed a physical map of the plasmid was constructed. For that purpose first a map of the Inc.P-1 type plasmid R772 was composed (FIG. 1). Thereupon a transposition element was identified and isolated from R772, (FIG. 2). Finally, a physical map for the plasmid pAL969 was composed, in which more or less intact copies of the transposition element are indicated (FIG. 3).

10 Different restriction endonucleases were tested with R772 DNA. It appeared that three of them, to wit BglII, KpnI and ZbaI, could not cut the plasmid open, whilst the restriction enconucleases BamHI cut the plasmid open at one site. The other restriction enzymes, to wit HpaI, SalI, SmaI, HindIII, EcoRI and PstI cut the plasmid at various sites. From the following table B the number of recognition sites and fragment lengths can be read:

TABLE B

Length of restriction endonucleases fragments of R7772 (in Mdalton).

| Enzyme fragment | BamHI | HpaI | SalI | SmaI | HindIII | EcoRI | PstI |
|---|---|---|---|---|---|---|---|
| 1 | 40.5 | 23.0 | 13.0 | 20.4 | 19.8 | 19.1 | 18.3 |
| 2 | | 16.1 | 11.6 | 12.5 | 10.7 | 6.4 | 9.0 |
| 3 | | 1.4 | 8.9 | 4.4 | 6.0 | 6.4 | 4.7 |
| 4 | | | 7.0 | 2.7 | 4.0 | 5.8 | 4.4 |
| | | | | 0.5 | | 1.8 | 2.4 |
| | | | | | | 1.0 | 1.7 |

The size of the R772 DNA appeared to be 40.5 Mdalton. The unique BamHI place was selected as origin (reference point) on the map. The order of the fragments could not yet be established unambiguously after double digestions. That is why individual HindIII and SalI restriction fragments of R772 were isolated from the gel, labelled in vitro with $^{32}$p, and hydridised on bolts which contain R772 DNA, which was digested with all rstriction enzymes investigated. From the position of hydridising fragments, obeserved on autoradiograms, a provisional circular map of R772 could be constructed. As many restriction endonuclease recognition sites were positioned so close to each other that the order could not yet be established unambiguously, particular restriction fragments of R772 were cloned on multicopy plasmids. The PstI fragments 6 and 3 were cloned on pBR325, and the HindIII fragments, 4, 3, 4+3 and 1+2 were cloned on the vector pTR262 in which gene activation can occur after insertion (described by Roberts et al, Gene 12, 123–127 (1980)). By using these clones in restriction endonuclease analysis most of the recognition sites could be mapped accurately. Only the EcoRI fragments 5 and 6 and the PstI fragments 4 and 5 could not be arranged, because they were neighbours and do not contain restriction sites of the other restriction enzymes (vide FIG. 1).

The cloning experiments also gave some information on the position of particular genetic properties, that was not yet known for plasmid R772. From the HindIII cloning experiment on pTR262 it turned out that neither HindIII fragment 4 not HindIII fragment 3 contained an intact kanamycin resistance $Km^r$-locus (the only marker for antibiotic resistance of the plasmid R772), whilst in case of combined cloning of these HindIII fragments 3+4 as one segment with maintenance of the original orientation kanamycin resistance found expression. This seemed to be an indication that the $Km^r$-locus overlaps the HindIII recognition site in this segment consisting of th fragments 3 and 4. This was confirmed by cloning of EcoRI fragments of R772 and pBR322, in that EcoRI fragment 2 appeared to contain the $Km^r$-locus. In these EcoRI cloning experiments also a plasmid was found which only contained the $Km^r$ determinant and no pBR322 markers. This plasmid (pRL236) appeared to consist of the EcoRI fragments 1 and 2 of R772 which is an indication that these two fragments together contained all information required for autonomous replication. As this plasmid pRL236 appeared to be transfer deficient, tra functions must be in the region of the EcoRI fragments 3, 4, 5 or 6. A clone pRL238 consisting of pTR262 and the HindIII fragments 1 and 2 of R772 appeared to be $tra^+$ and be able to replicate in Agrobacterium. As the pTR262 replicator does not work in Agrobacterium consequently the HindIII fragments 1 and 2 of R772 must contain all the information required for auto-transfer and autonomous replication. The replication and incompatibility functions of R772 must therefore be in Hind fragment 1.

(Abbreviatins used: tra for functions which are required for autotransfer by conjugation; ori for origin of replication; inc for incompatibility functions).

In the article by Hooykaas et al, Plasmid 4, 64–75 (1980) earlier mentioned it is indicated that mobilised Ti plasmids of *A. tumefaciens* carry an insertion sequence or transposon which originates from the mobilising plasmid. If it is assumed that mobilisation proceeds via cointegrate formation as a result of transposition, the prsence of two directly repeated copies of a transposition element in an unstable intermediary product is expected. The instability is the result of homologous recombination between the two intact copies of the transposition element, in consequence of which the cointegrate would desintegrate in its components. In order to be able to understand the stability of the cointegrate plasmid pAL969, the position and the structure of copies of the transposition element have been investigated.

A transposition elemen identified for R772 was isolated on pBR322. The plasmid in question (pRL246) was analysed, and it appeared that the transposition element did not contain the only antibiotic resistance marker of R772 ($Km^r$), so that the transposition element can be called an insertion sequence (called IS70). Homoduplex analysis of plasmid pRL246 revealed that IS70 carried short inverted repeats at its extremities having a length of about 50 base pairs (not shown). By means of restriction endonucleases the 2,5 Mdalton long IS70 was mapped on pBR322 (FIG. 2). By means of this map the position of IS70 in R772 could be indicated accurately (vide FIG. 1).

For the R772::Ti cointegrate plasmid pAL969 the position of cointegration beteen R772 and the Ti plasmid was determined by means of six different restriction endonucleases. The results are listed in the following table C.

TABLE C

| Position of cointegration in R772 and in pTIB6 for the R772::pTiB6 cointegrate | | |
|---|---|---|
| enzyme | cointegration took place in fragment R772 | fragment pTiB6 |
| BamHI | 1 | 15 |
| SmaI | 4 | 5 |
| HpaI | 1 | 10 |
| HindIII | 4 | 28 A |
| EcoRI | 2 | 16 |
| PstI | 3 | * |

*not determined

From these results it could be derived that the position of cointegration on R772 is present in a 1.5 Mdalton fragment (the part which overlaps SmaI fragment 4 and PstI fragment 3, vide FIG. 1) and on the Ti plasmid is present in a 0.8 Mdalton fragment (EcoRI fragment 16 and HindIII fragment 28A). When comparing the 1.5 Mdalton fragment on R772, in which cointegration had taken place, with the map of R772 it is apparent that this fragment carries part of the insertion sequence IS70, which makes one to assume that the cointegration indeed occurred via IS70.

When the cointegrate plasmid pAL969 would be cleaved with a restriction enzyme which does not have a recognition site in IS70, one would expect to find two fragments, which show sequence homology with IS70, to wit the two R772::Ti fusion fragments; in case of cutting with a restrcition enzyme, which has one recognition plase in IS70, one would expect to find four fragments with sequence homology with IS70; taken all this together assuming that the cointegrate plasmid contains two complete copies of IS70.

In practice this appeared not to be correct. The plasmid pBR322::IS70 (pRL246) was labelled in vitro and hybridised on blots which contained separate pA1969 DNA digested with different restrcition enzymes. In cases in which a restriction enzyme was used which does not have a recognition site in IS70 (EcoRI, HpaI), as expected, two different bands were observed on the autoradiograms. When using the restriction enzyme SmaI, which has one recognition site in IS70, however, not four but onle three bands were observed.

It appears from the results that the cointegratoin of R772 and the Ti plasmid took place via IS70, because the IS70 appeared to be present in duplicate. Apparently there only is one intact copy of IS70 whereas the other fragment is a deleted IS70. The length of the deleted IS70 is estimated to be at most 0.5 Mdalton. Furthermore, it can be concluded from the sum of the lengths of the fusion fragments of the cointegrate that a small piece of DNA of at most 0.5 Mdalton in the pTi component must have been deleted, although none of the restriction places investigated got lost.

The map of pAL969 with indication of IS70, the deleted IS70 and the $Km^r$locus constructed on the basis of these data is shown in FIG. 3. Fragments originating from R772 are provided with an asterisk.

The remarkable stability of pAL969 can now be explained by accepting that the length of the incomplete second copy of IS70 is not sufficient to make possible an efficient homologous recombination, which would lead to dissociation of the cointegrate into its composite plasmid.

B. Model experiment for site directed mutation of R772

A model experiment was designed for examining the application of the stable cointegrate pAL969 for site directed mutation in *E. coli*. Because of the realtively small size of R772 (40.5 Mdalton) modifications in the restriction patterns of a mutated R772 plasmid could be interpreted more easily than with the cointegrate plasmid, which has a size of 162 Mdalton. That is why first a site directed mutation was introduced in R772, characterised in it and only then introduced into the plasmid pAL969.

Figure 4:
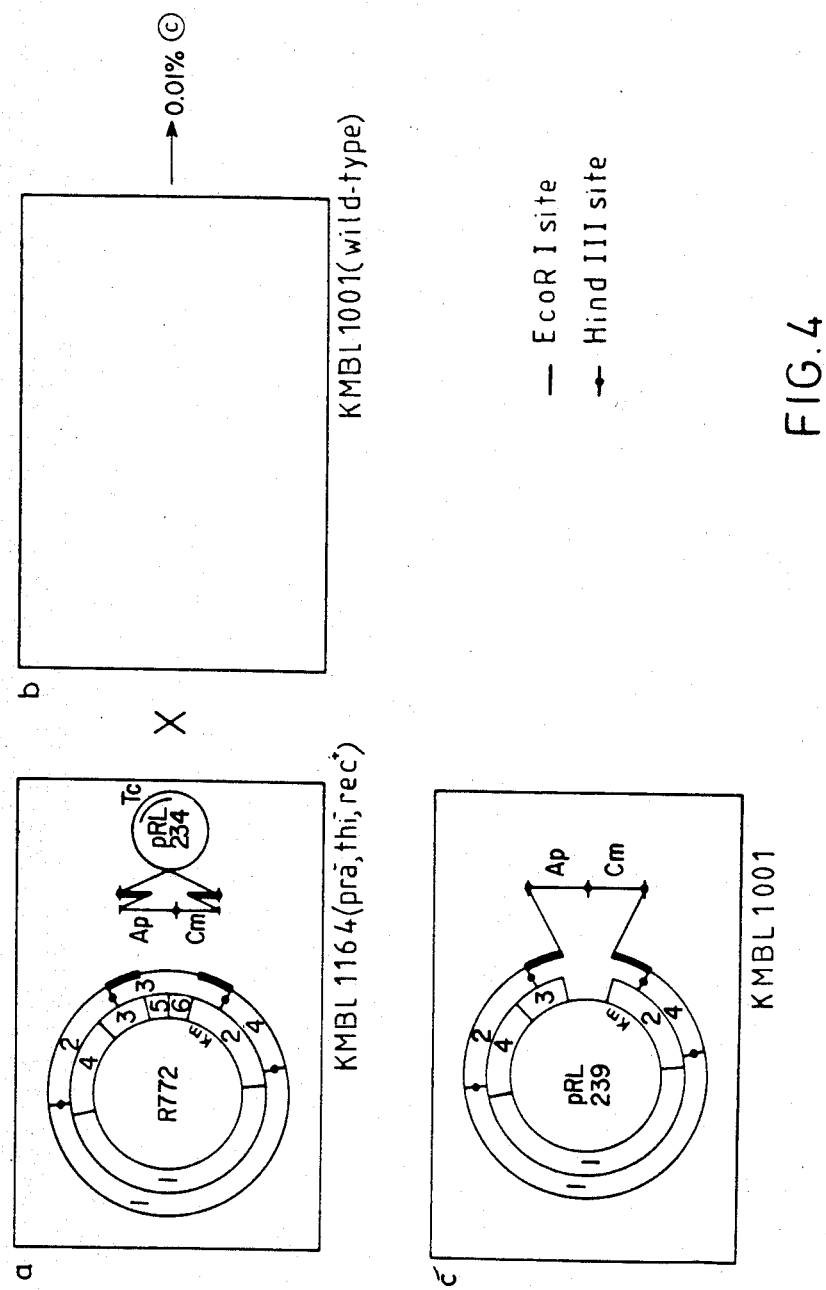
FIG. 4 illustrates in outline a model experiment for site directed mutations of R772.

The HindIII fragment 3 of R772 (length 6 Mdalton) was cloned on the vector pTR262 in which gene activation can occur after insertion. This fragment does not contain functions which are essential for auto-transfer or autonomous replication of R772. The resulting plasmid pRL232 has 3 EcoRI recognition sites which are all of them present in the cloned fragment: the vector part (pTR262) has no EcoRI sites. The two small internal EcoRI fragments of pRL232 (lengths resp. 1.8 and 1.0 Mdalton) were removed and replaced by an EcoRI fragment (total length 5.8 Mdalton) of the plasmid pRL220, which fragment contained ampicillin (Ap) and chloroamphenicol (Cm) resistance determinants. Thus a plasmid pRL234 was obtained which had Ap, Cm and Tc (tetracycline) resistant loci (vide FIG. 4a). On both sides of the $A_p{}^rCm^r$ fragment there was a segment, about 1.5 Mdalton long, with sequence homology with regard to R772 (thick lines in FIG. 4).

R772 and pRL234 were combined in one bacterial cell (KMBL1164) in order ro effect transfer of the $Ap^RCm^R$ segment to R772 via homologous recombination (vide FIG. 4a). This strain was then used as a donor in a crossing with KMBL100 (vide FIG. 4b). The transfer Inc.P-1 plasmid R772 was hig; about 1% of the recipient bacteria received this plasmid. In older experiments it has turned out that R772 mobilises the plasmid pBR322 with a frequency of $10^{-5}$ per transferred R772 (via IS70 of R772). Consequently it was expected that R772 would mobilise also the plasmid pRL234 via IS70 with a frequency of about $10^{-5}$. Actually, however, a transfer value for the $Ap^r$ determinant or $10^{-2}$ per transferred R772 was observed, much higher than expected for mobilisation by means of a transposition eccurrence. The high transfer frequency is presumably caused by the homology between pRL234 and R772.

For further analysis 22 $Ap^r$ colonies were selected; 14 thereof were $Ap^r$, $Cm^r$, $Km^r$, $Tc^r$ and 8 thereof were $Ap^r$, $Cm^r$, $Km^r$ and $Tc^s$. The set of 14 colonies showed expression of all markers both of R772 and of pRL234, from which it appeared that the complete pRL234 was mobilised (mobilisation frequency $6.5 \times 10^{-3}$ per transferred R772). The set of 8 colonies, however, carried the R772 marker ($Km^r$) and the $Ap^r$ and $Cm^r$ markers of the mutated HindIII fragment 3 of R772, but not the marker of the vector plasmid ($Tc^r$). These 8 colonies therefore seemed to have received the site directed mutation through insertion of the $Ap^rCm^r$ segment (replacement frequency $3.5 \times 10^{-3}$ per transferred R772). Plasmid DNA was isolated from three independent colonies and analysed via agarose gels; for all three only one plasmid of the same size was observed. The pattern of fragments obtained by digestion with HindIII was identical for these plasmids; the fragment 4 typical of a HindIII digestion of R772 had disappeared, whereas two new fragments were visible. These two new fragments were identical to the mutated HindIII fragment 3 of R772 in pRL234. In the plasmid pRL239 derived from R772 (vide FIG. 4c) no band of the vector plasmid pTR262 was found. So R772 was indeed mutated in a site directed mutation.

The same mutation was introduced into the cointegrate plasmid pAL969 in a similar manner. The results essentially corresponded to those obtained when using R772 and transferring a thus mutated R772::Ti cointegrate plasmid in *A. tumefaciens* bacteria and infecting plants therewith appeared to cause formation of normal tumours. This is in conformity with expectations, because the mutation was not localised in the Ti component of the cointegrate plasmid.

EXAMPLE

The suitability of the procedure described for site directed mutation of the T-region of the Ti component of the cointegrate plasmid pAL969 was investigated by cloning a fragment of the T-region (EcoRI fragment 7, vide FIG. 3) on the vector pACYC184. The plasmid pRAL3501 received contained two PstI recognition sites. The 0.5 Mdalton long PstI fragment was replaced by a 2.7 Mdalton long fragment with a $Cm^r$ determinant, which fragment was originating from the plasmid pRL220. On both sides of the segment containing the $Cm^r$ determinant there were pieces of DNA having lengths of resp. 2.5 and 1.8 Mdalton, which had sequence homology with the T-region. This mutation was then introduced into the cointegrate plasmid pAL969 in the was described earlier. Mutation was introduced into the pAL969 with a frequency of one to three $Cm^r$ transconjugants. One mutated pAL969 plasmid, called pAL1831, was isolated and digested with different restriction endonucleases, whereupon the fragment patterns were investigated by means of agarose gel electrophoresis. Herein it was confirmed that the 0.5 Mdalton PstI fragment of pAL969 in pAL1831 was replaced by a 2.7 Mdalton PstI fragment.

When the position of the foreign 2.7 Mdalton PstI fragment present in pAL1831 is replaced compared with the genetic maps of the T-region (vide Garfinkel et al, Cell 27, 143–153 (1981) and Ooms et al, Gene 14, 33–50 (1981) the mutation appears to be in the locus which causes a cyclokinin like effect. Compared with the transcription map of the T-region (vide Willmitzer et al, The Embo Journal 1, 139–146 (1982) transcript 4 is mutated.

The cointegrate plasmid pAL1831 was transferred from *E. coli* to *A. tumefaciens*, whereupon for one of the transcojugants the tumour inducing capacity with different plant species was studied. Unlike tumours induced by wild type octopine strains, the small tumours, which are induced by pAL1831 containing Agrobacterium bacteria on tobacco, developed roots. Also on Kalanchoë stems more than a normal root formation from tumours was observed. On tomatoes only small tumours were formed. These observations were in full agreement with the known phenotype of such mutations.

Figure 5:
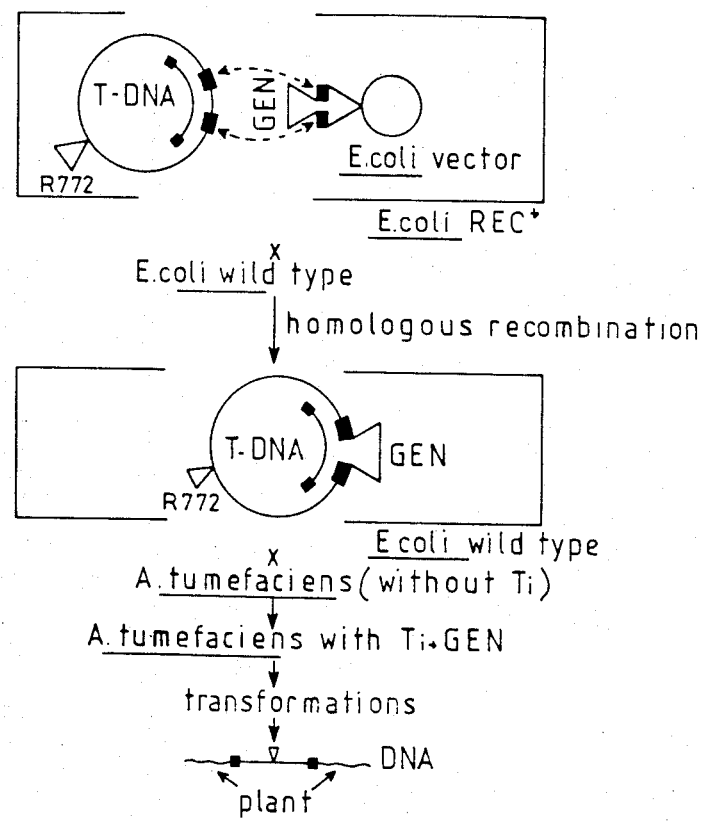
FIG. 5 shows in outline the procedure according to the invention for the incorporation of a foreign gene into the T-region of the Ti plasmid of *A. tumefaciens* and into the genome of dicotyledonous plants.

The procedure followed is represented in outline in FIG. 5.

FIG. 6 gives a picture of an octopine Ti plasmid, subdivided in a part responsible for tumour induction and a part responsible for the catabolism of octopine (octopine catabolism gene Occ) and arginine (arginine catabolism gene Arc). Tra, Inc and Rep are functions for resp. conjugation, incompatibility and replication. Aux, Cyt and Ocs are loci for resp. auxine and cytokine-like effects and octopine synthesis in the tumour cell.

FIG. 7 shows in larger detail the structure of the T-region of octopine Ti plasmids, after incorporation in the plant genome. At the extremities of the T-region there is a special base sequence of about 32 base pairs (bp), which are involved in the transfer and integration of T-DNA in the plant genome. Also, an "artificial" T-DNA, incorporated in the plant genome, is shown which contains one or more desirable genes and a marker gene for the selection of transformants. In order to make expression of these genes in the plant cell possible, special base sequences are present, including a plant promotor (Pp) as a starting place for the transcription in RNA (→), which see to the regulation of the gene expression in eucaryotes.

We claim:

1. A process for the incorporation of foreign DNA into the genome of dicotyledonous plants comprising infecting the plants or incubating plant protoplasts with *Agrobacterium tumefaciens* bacteria, which contain one or more Ti (tumour inducing) plasmids, characterized in that as Ti plasmid a stable cointegrate plasmid composed of the plasmid R772 and the plasmid pTiB6 with foreign DNA incorporated in the T-region of the Ti component of the cointegrate plasmid is applied.

2. A process as in claim 1, wherein the dicotyledonous plant cells or plant protoplasts with incorporated foreign DNA are cultured, and the product encoded by said foreign DNA is isolated.

3. A process for the production of *Agrobacterium tumefaciens* bacteria, which contain one or more Ti plasmids, comprising combining in *Escherichia coli* a vector known per se for use in *Escherichia coli*, provided with T-DNA region in which foreign DNA has been incorporated, with cointegrate plasmid pAL969 and the cointegrate plasmid with foreign DNA incorporated by double crossing-over in the T-region of the Ti component of transferring the cointegrate plasmid to *A. tumefaciens*.

* * * * *